(12) United States Patent
Paik et al.

(10) Patent No.: US 9,718,711 B2
(45) Date of Patent: Aug. 1, 2017

(54) METHODS AND APPARATUSES FOR FILTERING WATER FLUID BY SCREENING IONIC MINERALS

(71) Applicant: The Board of Trustees of the Leland Stanford Junior University, Palo Alto, CA (US)

(72) Inventors: Kee-Hyun Paik, Santa Clara, CA (US); Yang Liu, San Jose, CA (US); Robert W. Dutton, Palo Alto, CA (US); Qiushi Ran, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 421 days.

(21) Appl. No.: 14/043,732

(22) Filed: Oct. 1, 2013

(65) Prior Publication Data
US 2014/0174928 A1 Jun. 26, 2014

Related U.S. Application Data

(60) Provisional application No. 61/708,510, filed on Oct. 1, 2012.

(51) Int. Cl.
*C02F 1/46* (2006.01)
*C02F 1/469* (2006.01)
(Continued)

(52) U.S. Cl.
CPC .......... *C02F 1/4698* (2013.01); *B01D 63/088* (2013.01); *B01D 71/02* (2013.01);
(Continued)

(58) Field of Classification Search
CPC ...... B01D 61/422; B01D 61/44; B01D 61/46; B01D 61/50; B01D 61/54
See application file for complete search history.

(56) References Cited

U.S. PATENT DOCUMENTS

| 2,636,852 A | * | 4/1953 | McRae | .................... B01J 47/08 204/263 |
| 5,082,564 A | | 1/1992 | Halff et al. | |

(Continued)

OTHER PUBLICATIONS

Nam, S. W.; Rooks, M. J.; Kim, K. B.; Rossnagel, S. M. Ionic Field Effect Transistors with Sub-10 nm Multiple Nanopores. Nano Lett. 2009, 9, 2044-2048 Abstract Only.
(Continued)

*Primary Examiner* — Keith Hendricks
*Assistant Examiner* — Salil Jain
(74) *Attorney, Agent, or Firm* — Crawford Maunu PLLC

(57) ABSTRACT

Various aspects of the present disclosure are directed toward apparatus and methods method for filtering water fluid by screening ionic minerals including sodium chloride from the water fluid. In one embodiment, the water fluid is passed into a work zone defined at least in part by oppositely-arranged first and second porous structures, each of which have a plurality of gated channels. The water fluid is processed in the work zone by applying respective electric voltages to electrically bias the first porous structure and the second porous structure. The respective electric voltages deplete sodium chloride ions in the water fluid in the work zone due to ion-flux continuity. In response to processing of the water fluid, ion-filtered water is collected from the work zone.

21 Claims, 7 Drawing Sheets

(51) Int. Cl.
*B01L 3/00* (2006.01)
*B01D 63/08* (2006.01)
*B01D 71/02* (2006.01)
*G01N 33/487* (2006.01)

(52) U.S. Cl.
CPC ........... *B01L 3/502761* (2013.01); *B01L 3/56* (2013.01); *B01L 3/502738* (2013.01); *B01L 3/502753* (2013.01); *B01L 2200/0647* (2013.01); *B01L 2300/0864* (2013.01); *B01L 2400/0418* (2013.01); *B01L 2400/0421* (2013.01); *B01L 2400/0487* (2013.01); *B01L 2400/0627* (2013.01); *G01N 33/48721* (2013.01)

(56) References Cited

U.S. PATENT DOCUMENTS

| | | | |
|---|---|---|---|
| 5,223,107 A * | 6/1993 | Batchelder | A23C 9/144 204/527 |
| 6,413,792 B1 | 7/2002 | Sauer et al. | |
| 7,001,792 B2 | 2/2006 | Sauer et al. | |
| 2003/0211502 A1 | 11/2003 | Sauer et al. | |
| 2005/0252857 A1* | 11/2005 | Wilson | B01D 61/44 210/650 |
| 2006/0049105 A1 | 3/2006 | Max | |
| 2006/0154399 A1 | 7/2006 | Sauer et al. | |
| 2008/0057398 A1* | 3/2008 | Wei | B01D 61/44 429/218.1 |
| 2008/0119366 A1 | 5/2008 | Sauer et al. | |
| 2009/0314718 A1 | 12/2009 | Sparrow et al. | |
| 2011/0147314 A1 | 6/2011 | Kippeny et al. | |
| 2012/0031763 A1* | 2/2012 | Ohmi | B01D 61/46 204/633 |
| 2012/0097539 A1* | 4/2012 | Qian | G01N 33/48721 204/451 |
| 2013/0034489 A1 | 2/2013 | Gilliam et al. | |

OTHER PUBLICATIONS

Vermesh, U.; Choi, J. W.; Vermesh, O.; Fan, R.; Nagarah, J.; Heath, J. R. Fast Nonlinear Ion Transport via Field-Induced Hydrodynamic Slip in Sub-20-nm Hydrophilic Nanofluidic Transistors. Nano Lett. 2009, 9, 1315-1319.
H.-C. Chang and G. Yossifon, "Understanding electrokinetics at the nanoscale: A perspecrive", Biomicrofluidics, 012001 (2009).
E. C. Yusko, R. An, and M. Mayer, "Electroosmotic Flow Can Generate Ion Current Rectification in Nano- and Micropores". ACS Nano, p. 477 (2010).
Liu, Y.; Huber, D. E.; Dutton, R. W. Limiting and Overlimiting Conductance in Field-Effect Gated Nanopores. Appl. Phys. Lett. 2010, 96, 253108.
S.J. Kim, S.H. Ko, K. H. Kang and J. Han, "Direct seawater desalination by ion concentration polarization," Nature Nanotechnology, vol. 5, pp. 297-301 (Apr. 2010).
Garaj, S.; Hubbard, W.; Reina, A.; Kong, J.; Branton, D.; Golovchenko, J. A. Graphene as a Subnanometre Trans-Electrode Membrane. Nature 2010, 467, 190-194.
Liu, Y.; Huber, D. E.; Tabard-Cossa, V.; Dutton, R. W. Descreening of Field Effect in Electrically Gated Nanopores. Appl. Phys. Lett. 2010, 97, 143109.
Firnkes, M.; Pedone, D.; Knezevic, J.; Doblinger, M.; Rant, U Electrically Facilitated Translocations of Proteins through Silicon Nitride Nanopores: Conjoint and Competitive Action of Diffusion, Electrophoresis, and Electroosmosis. Nano Lett. 2010, 10, 2162-2167.
Stein, D.; Deurvorst, Z.; van der Heyden, F. H. J.; Koopmans, W. J. A.; Gabel, A.; Dekker, C. Electrokinetic Concentration of DNA Polymers in Nanofluidic Channels. Nano Lett. 2010, 10, 765-772.
Wanunu, M.; Morrison, W.; Rabin, Y.; Grosberg, A. Y.; Meller, A. Electrostatic Focusing of Unlabelled DNA into Nanoscale Pores Using a Salt Gradient. Nat. Nanotechnol. 2010, 5, 160-165.
Luan, B. Q.; Peng, H. B.; Polonsky, S.; Rossnagel, S.; Stolovitzky, G.; Martyna, G. Base-by-Base Ratcheting of Single Stranded DNA through a Solid-State Nanopore. Phys. Rev. Lett. 2010, 104, 238103.
Muthukumar, M. Theory of Capture Rate in Polymer Translocation. J. Chem. Phys. 2010, 132, 195101.
Kowalczyk, S. W.; Grosberg, A. Y.; Rabin, Y.; Dekker, C. Modeling the Conductance and DNA Blockade of Solid-State Nanopores. Nanotechnology 2011, 22, 315101.
Albrecht, T. How to Understand and Interpret Current Flow in Nanopore/Electrode Devices. ACS Nano 2011, 5, 6714-6725. Abstract Only.
Sadki, E. S.; E. S.; Garaj S.; Vlassarev, D.; Golovchenko, J. A.; Branton, D. Embedding a Carbon Nanotube across the Diameter of a Solid State Nanopore. J. Vac. Sci. Technol., B 2011, 29, 053001.
Venkatesan, B. M.; Bashir, R. Nanopore Sensors for Nucleic Acid Analysis. Nat. Nanotechnol. 2011, 6, 615-624.
Yusko, E. C.; Johnson, J. M.; Majd, S.; Prangkio, P.; Rollings, R. C.; Li, J. L.; Yang, J.; Mayer, M. Controlling Protein Translocation through Nanopores with Bio-Inspired Fluid Walls. Nat. Nanotechnol. 2011, 6, 253-260.
Kowalczyk, S. W.; Kapinos, L.; Blosser, T. R.; Magalhaes, T.; van Nies, P.; Lim, R. Y. H.; Dekker, C. Single-Molecule Transport across an Individual Biomimetic Nuclear Pore Complex. Nat. Nanotechnol. 2011, 6, 433-438. Abstract Only.
Powell, M. R.; Cleary, L.; Davenport, M.; Shea, K. J.; Siwy, Z. S. Electric-Field-Induced Wetting and Dewetting in Single Hydrophobic Nanopores. Nat. Nanotechnol. 2011, 6, 798-802. Abstract Only.
Jin, X. Z.; Aluru, N. R. Gated Transport in Nanofluidic Devices. Microfluid. Nanofluid. 2011, 11, 297-306.
He, Y. H.; Tsutsui, M.; Fan, C.; Taniguchi, M.; Kawai, T. Gate Manipulation of DNA Capture into Nanopores. ACS Nano 2011, 5, 8391-8397. Abstract Only.
Xie, P.; Xiong, Q.; Fang, Y.; Qing, Q.; Lieber, C. M. Local Electrical Potential Detection of DNA by Nanowire-Nanopore Sensors. Nat. Nanotechnol. 2011, 7, 119-125.
Ivanov, A. P.; Instuli, E.; McGilvery, C. M.; Baldwin, G.; McComb, D. W.; Albrecht, T.; Edel, J. B. DNA Tunneling Detector Embedded in a Nanopore. Nano Lett. 2011, 11, 279-285.
Harrer, S.; Waggoner, P. S.; Luan, B. Q.; Afzali-Ardakani, A.; Goldfarb, D. L.; Peng, H. B.; Martyna, G.; Rossnagel, S. M.; Stolovitzky, G. A. Electrochemical Protection of Thin Film Electrodes in Solid State Nanopores. Nanotechnology 2011, 22, 275304.
Venkatesan, B. M.; Estrada, D.; Banerjee, S.; Jin, X. Z.; Dorgan, V. E.; Bae, M. H.; Aluru, N. R.; Pop, E.; Bashir, R. Stacked Graphene-Al2O3 Nanopore Sensors for Sensitive Detection of DNA and DNA_Protein Complexes. ACS Nano 2012, 6, 441-450.
L. Onsager and S. Kim, "Wien Effect in Simple Strong Electrolytes", J. Phys. Chem., 61 (2) pp. 198-215 (1957). First Page Only.
P. Bergveld, "A critical evaluation of direct electrical protein detection methods," Biosensors and Bioelectronics; 6 (1):55-72 (1991).
F. Danneville, H. Happy, G. Dambrine, J.-M. Belquin, A. Cappy, "Microscopic noise modeling and macroscopic noise models: how good a conection?", IEEE Trans. on Electron Devices, vol. 41, No. 5, pp. 779-786 (May 1994) Abstract Only.
Soderman, O.; Jonsson, B. Electro-Osmosis: Velocity Profiles in Different Geometries with Both Temporal and Spatial Resolution. J. Chem. Phys. 1996, 105, 10300-10311. Abstract Only.
J. J. Kasianowicz, E. Brandin, D. Branton, and D. W. Deamer, "Characterization of individual polynucleotide molecules using a membrane channel," Proc. Natl. Acad. Sci., vol. 93, No. 24, pp. 13770-13773 (1996).
E. Souteyrand, J.P. Cloarec, J.R. Martin, C. Wilson, I. Lawrence, S. Mikkelsen, M.F. Laurence, "Direct detection of the hybridization of synthetic homo-oligomer DNA sequences by field effect," J. Phys. Chem. B, vol. 101, pp. 2980-2985 (1997). Abstract Only.
B. Schasfoort, S. Schlautmann, J. Hendrikse, and A. van den Berg, "Field-Effect Flow Control for Microfabricated Fluidic Networks", Science, pp. 942-945 (1999). Abstract Only.

(56) References Cited

OTHER PUBLICATIONS

Jung-Suk Goo, Chang-Hoon Choi, F. Danneville, E. Morifuji, H.S. Momose, Yu Zhiping, H. Iwai, T.H. Lee, and R.W. Dutton, "An accurate and efficient high frequency noise simulation technique for deep submicron MOSFETs", IEEE Trans. on Electron Devices, vol. 47, No. 12, Dec. 2000, pp. 2410-2419 (2000).
S. Howorka, S. Cheley, and H. Bayley, "Sequence-specific detection of individual DNA strands using engineered nanopores," Nature Biotechnology, vol. 19, No. 7, pp. 636-639 (2001). Abstract Only.
J. Li, D. Stein, C. McMullan, D. Branton, M. Aziz, and J. Golovshenko, "Ion-beam sculpting at nanometer length scales," Nature, 2001; 412(6843):166-169 (2001).
Meller, L. Nivon, and D. Branton, "Voltage-driven DNA translocations through a nanopore," Physical Review Letters, vol. 86, No. 15, pp. 3435-3438 (2001).
G. De Geronimo, P. O'Connor, V. Radeka, B. Yu, "Front-end electronics for imaging detectors", Nuclear Instruments and Methods in Physics Research A 471 192-199 (2001).
Chun, K. Y.; Stroeve, P. Protein Transport in Nanoporous Membranes Modified with Self-Assembled Monolayers of Functionalized Thiols. Langmuir 2002, 18, 4653-4658. Abstract Only.
M. Shim, N. Wong Shi Kam, R. Chen, Y. Li, and H. Dai, "Functionalization of Carbon Nanotubes for Biocompatibility and Biomolecular Recognition," American Chemical Society, Nano Letters, Jan. 21, 2002.
M. J. Schoning and A. Poghossian, "Recent advances in biologically sensitive field-effect transistors (BioFETs)," Analyst, vol. 127, pp. 1137-1151 (2002).
W. Huang, S. Taylor, K. Fu, Y. Lin, D. Zhang, T. Hanks, A. Rao, and Y. Sun, "Attaching Proteins to Carbon Nanotubes via Diimide-Activated Amidation," American Chemical Society, Nano Letters, Mar. 16, 2002, 2 (4), pp. 311-314 Abstract Only.
P. Bergveld, "Thirty years of Isfetology: what happened in the past 30 years and what may happen in the next 30 years," Sensors and Actuators B, vol. 88, pp. 1-20 (2003). Abstract Only.
Nakane, J. J.; Akeson, M.; Marziali, A. Nanopore Sensors for Nucleic Acid Analysis. J. Phys: Condens. Matter 2003, 15, R1365—R1393. Abstract Only.
Dai, J. H.; Ito, T.; Sun, L.; Crooks, R. M. Electrokinetic Trapping and Concentration Enrichment of DNA in a Microfluidic Channel. J. Am. Chem. Soc. 2003, 125, 13026-13027.
A.J. Storm, J. Chen, X. Ling, and D.C. Zandbergen, "Fabrication of solid-state nanopores with single-nanometer precision," Nature Mater.; 2(8):537-540 (2003).
J. Hahm and C. M. Lieber, "Direct ultrasensitive electrical detection of DNA and DNA sequence variations using nanowire nanosensors," Nano Letters, vol. 4, No. 1, pp. 51-54 (2004).
Z. Li et al., "Sequence specific label-free DNA sensors based on silicon nanowires," Nano Letters, vol. 4, pp. 245-247 (2004).
Laser and Santiago, "A Review of Micropumps," J. Micromech. Microeng. 14 (2004) R35-R64.
Nawrocki, J.; Dunlap, C.; McCormick, A.; Carr, P. W.; Part, I. Chromatography Using Ultra-stable Metal Oxide-Based Stationary Phases for Hplc. J. Chromatogr., A 2004, 1028, 1-30. Abstract Only.
Karnik, R.; Fan, R.; Yue, M.; Li, D. Y.; Yang, P. D.; Majumdar, A. Electrostatic Control of Ions and Molecules in Nanofluidic Transistors. Nano Lett. 2005, 5, 943-948.
H. Daiguji, Y. Oka, and K. Shirono, "Nanofluidic Diode and Bipolar Transistor". Nano Letters, 2274 (2005). Abstract Only.
Meagher, R. J.; Won, J. I.; McCormick, L. C.; Nedelcu, S.; Bertrand, M. M.; Bertram, J. L.; Drouin, G.; Barron, A. E.; Slater, G. W. End-Labeled Free-Solution Electrophoresis of DNA. Electrophoresis 2005, 26, 331-350.
Chun, K. Y.;Mafe, S.; Ramirez, P.; Stroeve, P. Protein Transport through Gold-Coated, Charged Nanopores: Effects of Applied Voltage. Chem. Phys. Lett. 2006, 418, 561-564. Abstract Only.
Karnik, R.; Castelino, K.; Majumdar, A. Field-Effect Control of Protein Transport in a Nanofluidic Transistor Circuit. Appl. Phys. Lett. 2006, 88, 123114. Abstract Only.
M. C. Cheng et al., "Nanotechnologies for biomolecular detection and medical diagnostics," Current Opinion in Chemical Biology, vol. 10, pp. 11-19 (2006).
A. Talasaz M. Nemat-Gorgani, Y. Liu, P. Stahl, R.W. Dutton, M. Ronaghi, and R.W. Davis, "Prediction of protein orientation immobilization upon mmobilization on biological and nonbiological surfaces," Proc Natl Acad Sci, 103(40):14773-8 (2006).
E. Stern et al., "Label-free immunodetection with CMOS-compatible semiconducting nanowires," Nature, vol. 445, pp. 519-522 (2007).
Gracheva, M. E.; Vidal, J.; Leburton, J. P. p_n Semiconductor Membrane for Electrically Tunable Ion Current Rectification and Filtering. Nano Lett. 2007, 7, 1717-1722.
He, J.; Lin, L.; Zhang, P.; Lindsay, S. Identification of DNA Basepairing via Tunnel-Current Decay. Nano Lett. 2007, 7, 3854-3858.
A. Holtzel and U. Tallarek, "Ionic conductance of nanopores in microscale analysis systems: where microfluidics meets nanofluidics.", J. Sep. Sci., 1398 (2007). Abstract Only.
S. Kim, Y.-C. Wang, J. Lee, H. Jang, and J. Han, "Concentration Polarization and Nonlinear Electrokinetic Flow near Nanofluidic Channel", Phys. Rev. Lett., 044501 (2007).
Dekker, C. "Solid-State Nanopores." Nat. Nanotechnol. 2007, 2, 209-215, Abstract Only.
Branton, D.; Deamer, D. W.; Marziali, A.; Bayley, H.; Benner, S. A.; Butler, T.; Di Ventra, M.; Garaj, S.; Hibbs, A.; Huang, X. H.; et al. The Potential and Challenges of Nanopore Sequencing. Nat. Biotechnol. 2008, 26, 1146-1153.
Y. Liu, J. Sauer, and R. Dutton, "Effect of Electrodiffusion Current Flow on Electrostatic Screening in Aqueous Pores," J. Appl. Phys. 103, pp. 084701-1-03 (2008).
Y. Liu, K. Lilja, C. Heitzinger, and R. Dutton, "Overcoming the Screening-Induced Performance Limits of Nanowire Biosensors: A Simulation Study on the Effect of Electro-Diffusion Flow," Electron Devices Meeting, IEDM 2008, IEEE International, pp. 1-4 (2008).
P. R. Nair and M. A. Alam, "Screening-limited response of nanobiosensors," Nano Letters, vol. 8, No. 5, pp. 1281-1285 (2008).
C. Bouzigues, P. Tabeling, and L. Bocquet, "Nanofluids in the Debye Layer at Hydrophilic and Hydrophobic Surfaces", Phys. Rev. Lett., 101, 114503 (2008).
M. Gracheva, D. Melnikov, and J. Leburton, "Multilayered Semiconductor Membranes for Nanopore Ionic Conductance", ACS Nano, , 2349 (2008).
E. Kalman, I. Vlassiouk, and Z. Siwy, "Nanofluidic Bipolar Transistors", Advanced Materials, 293 (2008). Abstract Only.
R. Fan, S. Huh, R. Yan, J. Arnold, and P. Yang, "Gated proton transport in aligned mesoporous silica films" Nature Mater., 303 (2008).
Zhou, K. M.; Kovarik, M. L.; Jacobson, S. C. Surface-Charge Induced Ion Depletion and Sample Stacking near Single Nanopores in Microfluidic Devices. J. Am. Chem. Soc. 2008, 130, 8614-8616. Abstract Only.
Sparreboom, W.; van den Berg, A.; Eijkel, J. C. T. Principles and Applications of Nanofluidic Transport. Nat. Nanotechnol. 2009, 4, 713-720. Abstract Only.
E. Kalman, O. Sudre, I. Vlassiouk, and Z. Siwy, "Control of ionic transport through gated single conical nanopores", Anal. Nomal. Chem., 413 (2009).
M. Taniguchi, M. Tsutsui, K. Yokota, and T. Kawai, "Fabrication of the gating nanopore device". Appl. Phys. Lett., (2009). Abstract Only.
Tabard-Cossa, V.; Wiggin, M.; Trivedi, D.; Jetha, N. N.; Dwyer, J. R.; Marziali, A. Single-Molecule Bonds Characterized by Solid-State Nanopore Force Spectroscopy. ACS Nano 2009, 3, 3009-3014.

* cited by examiner

METHODS AND APPARATUSES FOR FILTERING WATER FLUID BY SCREENING IONIC MINERALS

BACKGROUND

Purification and/or desalination of a water fluid allows for the production of water that is safe for human consumption. Due to the large volumes of sea water and brackish water, as compared to the volumes of fresh water available on the earth, there may not always be an accessible and safe source of water for human consumption.

Purification and/or desalination of water is expensive and time consuming. Thus, there is a need for improved methods of producing water safe for human consumption.

SUMMARY

Various aspects of the present disclosure are directed toward controlling flow. More specifically, the present disclosure is directed toward filtering water fluid by screening ionic minerals.

Aspects of the present disclosure are directed toward methods for filtering water fluid by screening ionic minerals including sodium chloride from the water fluid. In these such methods, the water fluid is passed into a work zone defined at least in part by oppositely-arranged first and second porous structures. The first porous structure includes a plurality of gated channels, which correspond to an anode reservoir. Similarly, the second porous structure includes a plurality of gated channels, which correspond to a cathode reservoir. The water fluid is processed in the work zone by applying respective electric voltages to electrically bias the first porous structure and the corresponding anode reservoir with a first bias-polarity type. Additionally, applying respective electric voltages also electrically biases the second porous structure and the corresponding cathode reservoir with a second bias-polarity type that is opposite the first bias-polarity type. The respective electric voltages are set to establish a sufficient voltage difference therebetween to deplete sodium chloride ions in the water fluid in the work zone due to ion-flux continuity. Accordingly, sodium chloride anions are passed from the work zone through the gated channels of the first porous structure to the anode reservoir, and sodium chloride cations are passed from the work zone through the gated channels of the second porous structure to the cathode reservoir. In response to this processing, ion-filtered water is collected from the work zone.

Various aspects of the present disclosure are also directed toward water-filtering apparatuses. These apparatuses include a water processing station that processes water fluid having ionic minerals (including sodium chloride) in a work zone defined at least in part by oppositely-arranged first and second porous structures. The first porous structure includes a plurality of gated channels (corresponding to an anode reservoir), and the second porous structure includes a plurality of gated channels (corresponding to a cathode reservoir). The apparatuses also include an anode reservoir station and a cathode reservoir station. Additionally, the apparatuses include a power source that applies respective electric voltages, while the water fluid is in the work zone, to electrically bias the first porous structure with a first bias-polarity type and the second porous structure with a second bias-polarity type (opposite that of the first). Accordingly, the corresponding anode reservoir is also biased with the first bias-polarity type, and the cathode reservoir is also biased with the second bias-polarity type. The respective electric voltages are set to establish a sufficient voltage difference therebetween to deplete sodium chloride ions in the water fluid in the work zone due to ion-flux continuity. In this manner, sodium chloride anions are passed from the work zone through the gated channels of the first porous structure to the anode reservoir, and sodium chloride cations are passed from the work zone through the gated channels of the second porous structure to the cathode reservoir. A water collection station is included with the water-filtering apparatuses to receive the ion-filtered water from the work zone.

The above summary is not intended to describe each embodiment or every implementation of the present disclosure. The figures, detailed description and claims that follow more particularly exemplify various embodiments.

BRIEF DESCRIPTION OF THE DRAWINGS

The disclosure may be more completely understood in consideration of the detailed description of various embodiments of the disclosure that follows in connection with the drawings, each being consistent with one or more of these embodiments, in which.

Figure 1:
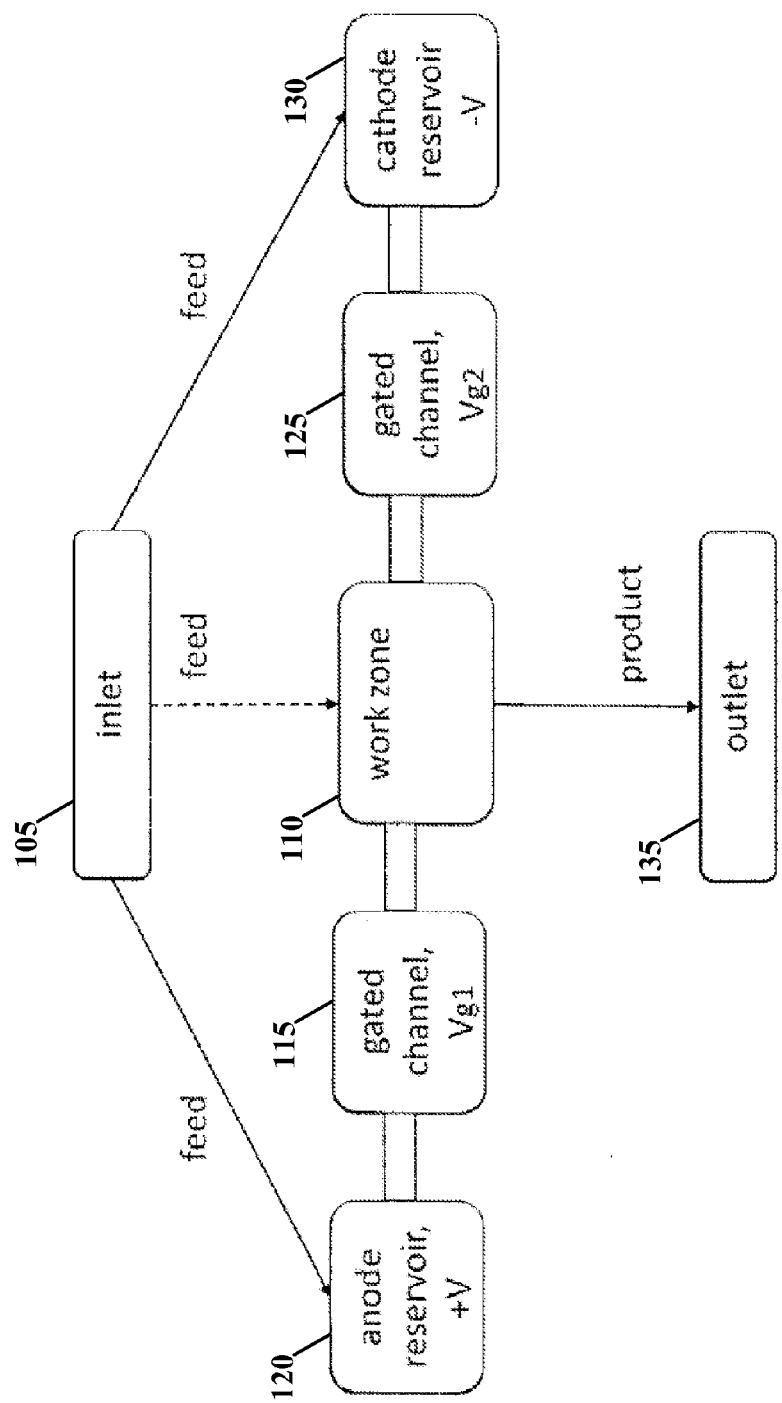
FIG. 1 shows an example device diagram for electrically modulating (increasing or decreasing) the concentration of positive and negative ionic species in a water solution, consistent with various aspects of the present disclosure.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims.

DESCRIPTION OF EMBODIMENTS

Various aspects of the present disclosure are directed toward apparatuses, methods, and systems useful in filtering water fluid by screening ionic minerals including sodium chloride from the water fluid.

More specifically, various aspects of the present disclosure are directed toward methods for filtering water fluid by screening ionic minerals including sodium chloride from the water fluid. These methods include passing the water fluid into a work zone defined at least in part by oppositely-arranged first and second porous structures. Both porous structures include sets of a plurality of gated channels that correspond, respectively, to an anode reservoir and a cathode reservoir. The methods also include processing the water fluid in the work zone. The water is processed by applying respective electric voltages to electrically bias the first porous structure and the corresponding anode reservoir with a first bias-polarity type and also to electrically bias the second porous structure and the corresponding cathode reservoir with a second bias-polarity type that is opposite the first bias-polarity type. The respective electric voltages are set to establish a sufficient voltage difference therebetween to deplete sodium chloride ions in the water fluid in the work zone due to ion-flux continuity. In this manner, sodium chloride anions are passed from the work zone through the plurality of gated channels of the first porous structure to the anode reservoir, and sodium chloride cations are passed from the work zone through the plurality of gated channels of the second porous structure to the cathode reservoir. In response to the step of processing, the methods include collecting ion-filtered water from the work zone.

In certain more specific embodiments, the methods also include the steps of providing water fluid in the cathode reservoir and anode reservoir during the step of processing the water fluid in the work zone, and providing the ion-filtered water from the work zone sufficiently desalinated or purified for human consumption. Additionally, in certain embodiments, the methods further include the step of replenishing the cathode reservoir and the anode reservoir with the water fluid to maintain a bulk ionic condition of the water fluid in each of the cathode reservoir and the anode reservoir. The methods can also include, in certain embodiments, a step of replenishing the cathode reservoir and the anode reservoir with the water fluid to maintain a bulk ionic condition of the water fluid in each of the cathode reservoir and the anode reservoir. Moreover, the step of replenishing the cathode reservoir and the anode reservoir with the water fluid can occur, in certain embodiments, by using a pressure differential that defines the pressure of the water fluid passed to the reservoirs relative to the pressure of the water fluid passed to the work zone to maintain a bulk ionic condition of the water fluid in each of the cathode reservoir and the anode reservoir. The porous structures, in certain embodiments of the methods for filtering water fluid, control particle electrophoresis through the pores and thereby maintain a range of ionic concentration in the work zone that falls within fifteen percent of a target range.

Additionally, in certain embodiments, the water fluid includes seawater manifesting sodium chloride at levels overlapping the range of 200-500 millimolar (mM), and the porous structures are sufficiently sized to pass the ions therethrough without clogging the porous structures. In other embodiments, the water fluid includes seawater manifesting sodium chloride at levels overlapping the range of 400-500 millimolar, and the porous structures are sufficiently sized to pass the ions therethrough without clogging the porous structures. In these such embodiments, the step of collecting includes providing the ion-filtered water with sodium chloride at levels in a range that is between 0.35 mM to 1.3 mM (e.g., 20-75 mg/L), and additionally, the methods include an additional step of filtering from the water fluid at least one of: oil droplets, macromolecules, biological ions, or ionic species including potassium.

In certain embodiments, the methods of the present disclosure include an inlet through which the water fluid is passed to the work zone, and an outlet at which ion-filtered water is collected, and further include processing the water fluid in the work zone by applying the respective electric voltages, in combination at least one of a pressure-difference control technique and electro-osmosis, to control particle electrophoresis through the pores and thereby maintain a selected concentration of sodium chloride ions in the work zone.

Additionally, in certain embodiments, applying the respective electric voltages includes controlling electrostatic potential within the pores and in the work zone via extended field effect that is not limited by the Debye screening length. In other embodiments, applying the respective electric voltages includes injecting the ionic minerals in the water fluid into the work zone at a faster rate than sodium chloride cations are passed from the work zone through the plurality of gated channels of the second porous structure. Moreover, applying the respective electric voltages can include injecting the ionic minerals in the water fluid into the work zone at a faster rate than sodium chloride anions are passed from the work zone through the plurality of gated channels of the first porous structure. Additionally, applying the respective electric voltages can include injecting the ionic minerals in the water fluid into the work zone at a faster rate than sodium chloride cations are passed from the work zone through the plurality of gated channels of the second porous structure and also at a faster rate than sodium chloride anions are passed from the work zone through the plurality of gated channels of the first porous structure.

Various aspects of the present disclosure are also directed towards water-filtering apparatuses. The water-filtering apparatuses include a water processing station that processes water fluid having ionic minerals therein including sodium chloride, in a work zone defined at least in part by oppositely-arranged first and second porous structures. The first porous structure includes a plurality of gated channels corresponding to an anode reservoir and the second porous structure includes a plurality of gated channels corresponding to a cathode reservoir. The water-filtering apparatuses also include an anode reservoir station and a cathode reservoir station. Further, the water-filtering apparatuses include a power source that applies respective electric voltages while the water fluid is in the work zone. This occurs by applying respective electric voltages to electrically bias the first porous structure (and the corresponding anode reservoir) with a first bias-polarity type and the second porous structure (and the corresponding cathode reservoir) with a second bias-polarity type that is opposite the first bias-polarity type. The respective electric voltages being set establish a sufficient voltage difference therebetween to deplete sodium chloride ions in the water fluid in the work zone due to ion-flux continuity. As a result, sodium chloride anions are passed from the work zone through the plurality of gated channels of the first porous structure to the anode reservoir, and sodium chloride cations are passed from the work zone through the plurality of gated channels of the second porous structure to the cathode reservoir. The water-filtering apparatuses also include a water collection station configured and arranged to receive the ion-filtered water from the work zone. In certain embodiments, the water-filtering apparatus filters from the water fluid at least one of: oil droplets, macromolecules, biological ions, or ionic species including potassium.

Turning now to the figures, FIG. 1 shows an example device diagram for electrically modulating (increasing or decreasing) the concentration of positive and negative ionic species in saline (water fluid) solutions, consistent with various aspects of the present disclosure. Water fluid is introduced at an inlet 105, and provided into a work zone 110 that is defined at least in part by oppositely-arranged first and second porous structures (shown in further detail in FIG. 2). The first porous structure is included at the first gated channel 115 corresponding to an anode reservoir 120, and the second porous structure is included at the second gated channel 125 corresponding to a cathode reservoir 130. The water fluid is processed in the work zone 110 by applying electric voltages to electrically bias the first porous structure and the corresponding anode reservoir 120 with a first bias-polarity type. Additionally, the water fluid is processed in the work zone 110 by also applying electric voltages to electrically bias the second porous structure and the corresponding cathode reservoir 130 with a second bias-polarity type that is opposite the first bias-polarity type. Based on the manner in which the bias is applied, the ionic species concentration can be increased or decreased at the outlet 135. Decreasing or increasing the ionic species concentration is discussed in further detail with reference to FIG. 3 and FIG. 4, respectively.

The ionic species in the water fluid can include, but are not limited to: 1) $Na^+$ and $Cl^-$ as in salt water; 2) biological ions or macromolecules in a biological-compatible solution with other ionic species ($Na^+$, $K^+$, $Cl^-$ etc.); and 3) other charged particles such as nano-particles, oil droplets, etc. Additionally, the size of the gated channels is not necessarily limited by the Debye screening length. The electrical biasing between anode and cathode drives ion transport in the transverse direction, which induces a de-screening effect and therefore enables effective gating of the gate electrodes. The dashed arrow indicates that the direct feeding from the inlet to the work zone is optional.

Figure 2:
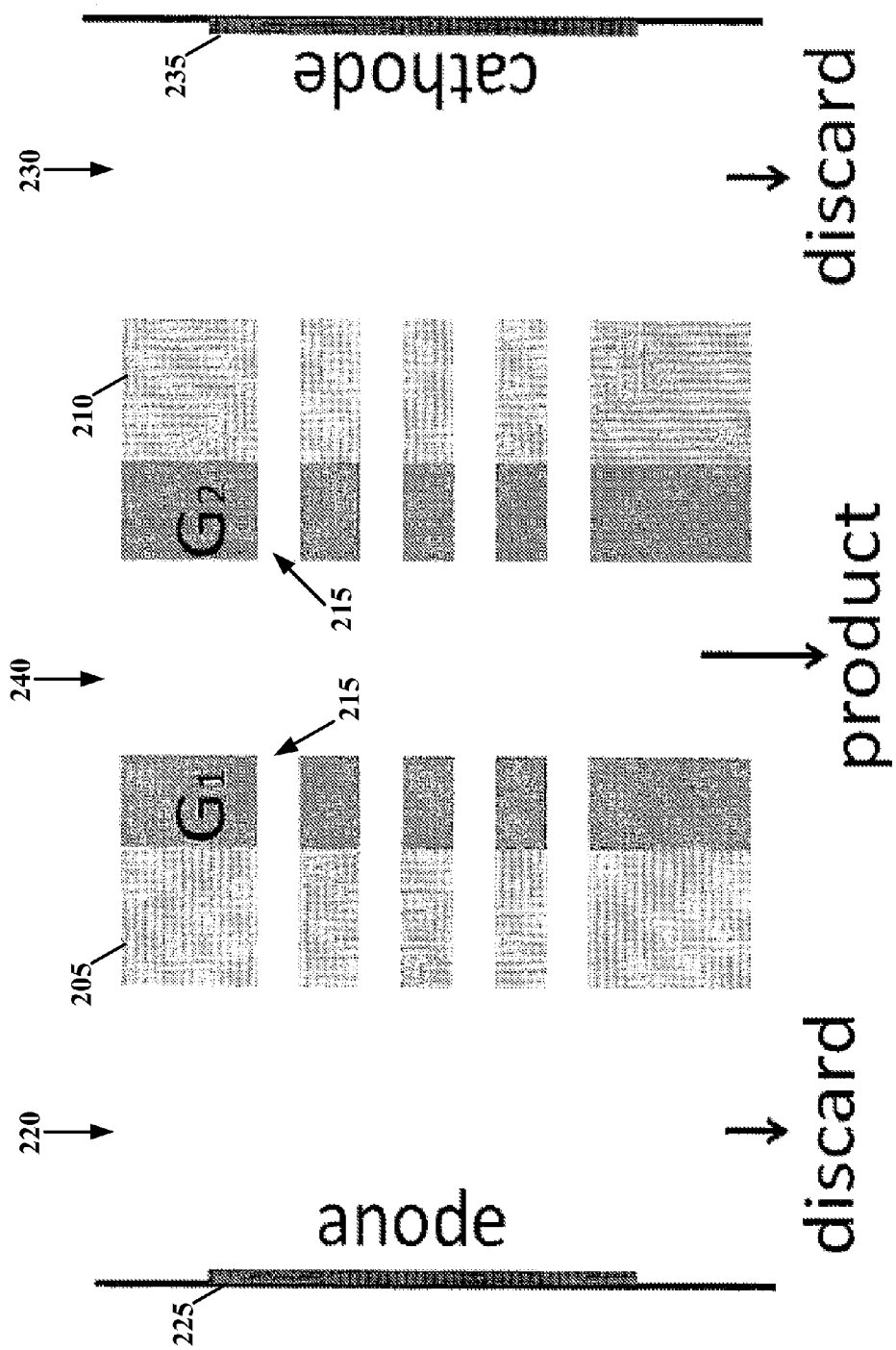
FIG. 2 shows an example device diagram for water-filtering, consistent with various aspects of the present disclosure.

FIG. 2 shows an example device diagram for water-filtering, consistent with various aspects of the present disclosure. FIG. 2 shows a more detailed version of a first porous structure 205 and a second porous structure 210 both of which includes a plurality of gated channels 215. The water-filtering device includes an anode reservoir 220 (with a respective anode 225) and a cathode reservoir 230 (with a respective cathode 235). In between the first porous structure 205 and the second porous structure 210 is a work zone 240. Water fluid, which includes ionic minerals such as sodium chloride, is passed through the work zone 240 and results in a product that includes the water fluid screened of ionic minerals. The screening occurs based on respective electric voltages set to establish a sufficient voltage difference between the anode reservoir 220 and the cathode reservoir 230 to deplete sodium chloride ions in the water fluid in the work zone 240 due to ion-flux continuity. In this manner, sodium chloride anions are passed from the work zone 240 through the plurality of gated channels 215 of the first porous structure 205 to the anode reservoir 220, and sodium chloride cations are passed from the work zone 240 through the plurality of gated channels 215 of the second porous structure 210 to the cathode reservoir 230. As a result, ion-filtered water is collected as a product from the work zone 240. The sodium chloride anions and the sodium chloride cations are discarded from the anode reservoir 220 and the cathode reservoir 230. In certain embodiments, other charged particles in the water-fluid are similarly filtered and discarded. These charged particles can include oil droplets, macromolecules, biological ions, or ionic species including potassium. Additionally, applying the respective electric voltages includes controlling electrostatic potential within the pores/gated channels 215 and in the work zone 240 via extended field effect that is not limited by the Debye screening length.

Figure 3:
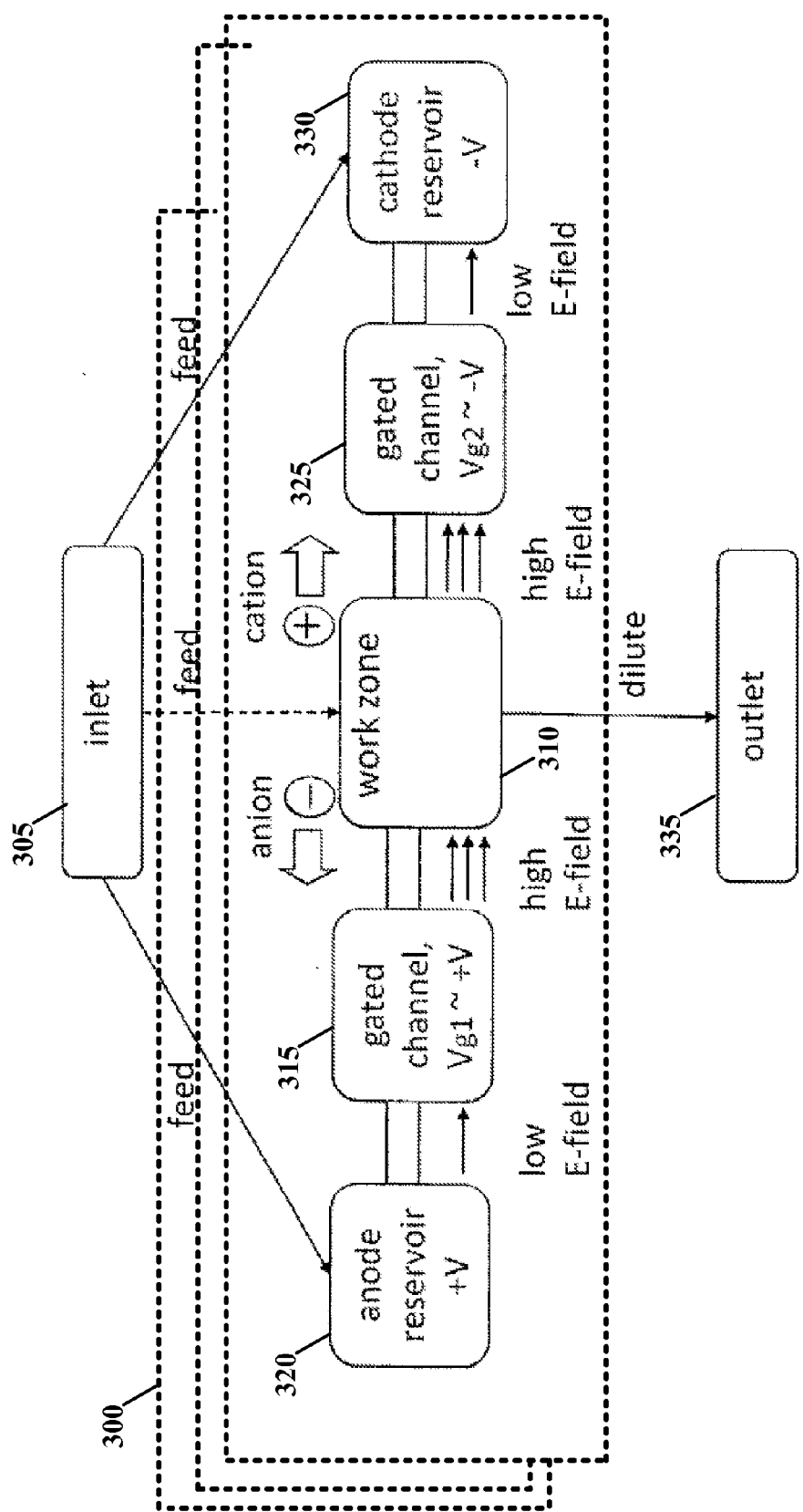
FIG. 3 shows an example diagram of a water-filtering apparatus, consistent with various aspects of the present disclosure.

FIG. 3 shows an example diagram of a water-filtering apparatus 300, consistent with various aspects of the present disclosure. Similar to the diagram shown in FIG. 1, water fluid is introduced at an inlet 305, and provided into a work zone 310. On opposing sides of the work zone 310, are a first gated channel 315 and a second gated channel 325 (each of which includes a porous structure as shown in further detail in FIG. 2). The first gated channel 315 connects the work zone 310 to an anode reservoir 320, and the second gated channel 325 connects the work zone 310 to a cathode reservoir 330.

The water fluid is processed in the work zone 310 by applying electric voltages to electrically bias the porous structure of the first gated channel 315 and the corresponding anode reservoir 320 with a first bias-polarity type ($V_{g1} \sim +V$). Additionally, the electric voltages are applied to electrically bias the porous structure of the second gated channel 325 and the corresponding cathode reservoir 330 with a second bias-polarity type that is opposite the first bias-polarity type ($V_{g2} \sim -V$). Due to this biasing, a high electric field is created between each of the work zone 310 and each of the gated channels 315/325. Further, a low electric field is respectively created between each of the gated channels 315/325 and the anode and cathode reservoirs 320/330. The electric voltages establish a sufficient voltage difference between the anode reservoir 320 and the cathode reservoir 330 to deplete sodium chloride ions in the water fluid in the work zone 310 due to ion-flux continuity. This is shown in FIG. 3 by the anions passing from the work zone 310, through the gated channel 315, and to the anode reservoir 320, while the cations are passing from the work zone 310, through the gated channel 325, and to the cathode reservoir 325. As a result, ion-filtered water is collected as product from the work zone 310 at the outlet 335. This depletion operation occurs due to the gate electrodes being biased so that a large potential drop occurs between them. The resultant high electric between the gates therefore leads to depletion of charged species within that zone due to ion flux continuity. As a result, desalination and/or purification of the water fluid occur.

The water fluid, as inlet to the example device shown in FIG. 3, can include seawater. The sodium chloride can manifest in the seawater at levels overlapping the range of 200-500 millimolar or, more specifically, 400-500 millimolar. Further, the porous structures, as shown in FIG. 2, of the gated channels 315/330 are sufficiently sized to pass the ions therethrough without clogging the porous structures. Additionally, the ion-filtered water collected at the outlet 335, in certain instances, has a sodium chloride concentration at levels in a range that is between 0.35 mM to 1.3 mM (or 20-75 mg/L). Biasing, as described with reference to FIG. 3, controls particle electrophoresis through the pores of the gated channels 315/330 and thus maintains a range of ionic concentration in the work zone 310 that falls within fifteen percent of a target range.

Multiple water-filtering apparatuses, consistent with various aspects of the present disclosure, can be connected in parallel to aid in the filtering of ionic species from a water fluid. This is shown in FIG. 3 by the inlet 305 and outlet 335 being connected between multiple water-filtering apparatuses 300 as is denoted by the dotted boxes surrounding the anode reservoir 320, the gated channels 315/325, the work zone 310, and the cathode reservoir 330. Additionally, the amount/volume of water-fluid filtered can depend on the number of water-filtering apparatuses that are connected in parallel. For instance, in certain embodiments, the water-filtering apparatuses and methods of the present disclosure can be implemented to filter water at a wide variety of flow rates, depending on the application. As examples, in smallervolume applications, such water-filtering apparatuses are implemented at a level directed to single-consumer use in which a few to several servings of water are filtered/desalinated over a period of several minutes to an hour, with the number of ounces per serving varying from one to several (8-ounce) cups. In higher-volume applications, such water-filtering apparatuses are implemented at an industrial level directed to providing filtered/desalinated industrial/human-consumable water in which many gallons of water are processed over a longer period time as might be tolerated to build up a reserve of industrial/human-consumable water that is drawn from as with a shared community resource. As the engineering and costs of such water-filtering apparatuses are optimized, over a few to several hours, the number of gallons would of course increase. For specific amounts and/or specific end-use applications, these water-filtering apparatuses are adaptable, as discussed above, to multiple apparatuses configured in parallel. As another example, such water-filtering apparatuses are implemented in parallel to increase volume and with a subset of the parallel apparatuses providing a lower-quality filtering for uses at the industrial level and other of the parallel apparatuses providing a higher-quality filtering for human-consumable water (with separate collection reservoirs to prevent mixing therebetween). Further, as illustrated and discussed with FIG. 6 below, a tiered arrangement of the water-filtering apparatuses provides for testing to ensure targeted water qualities.

Figure 4:
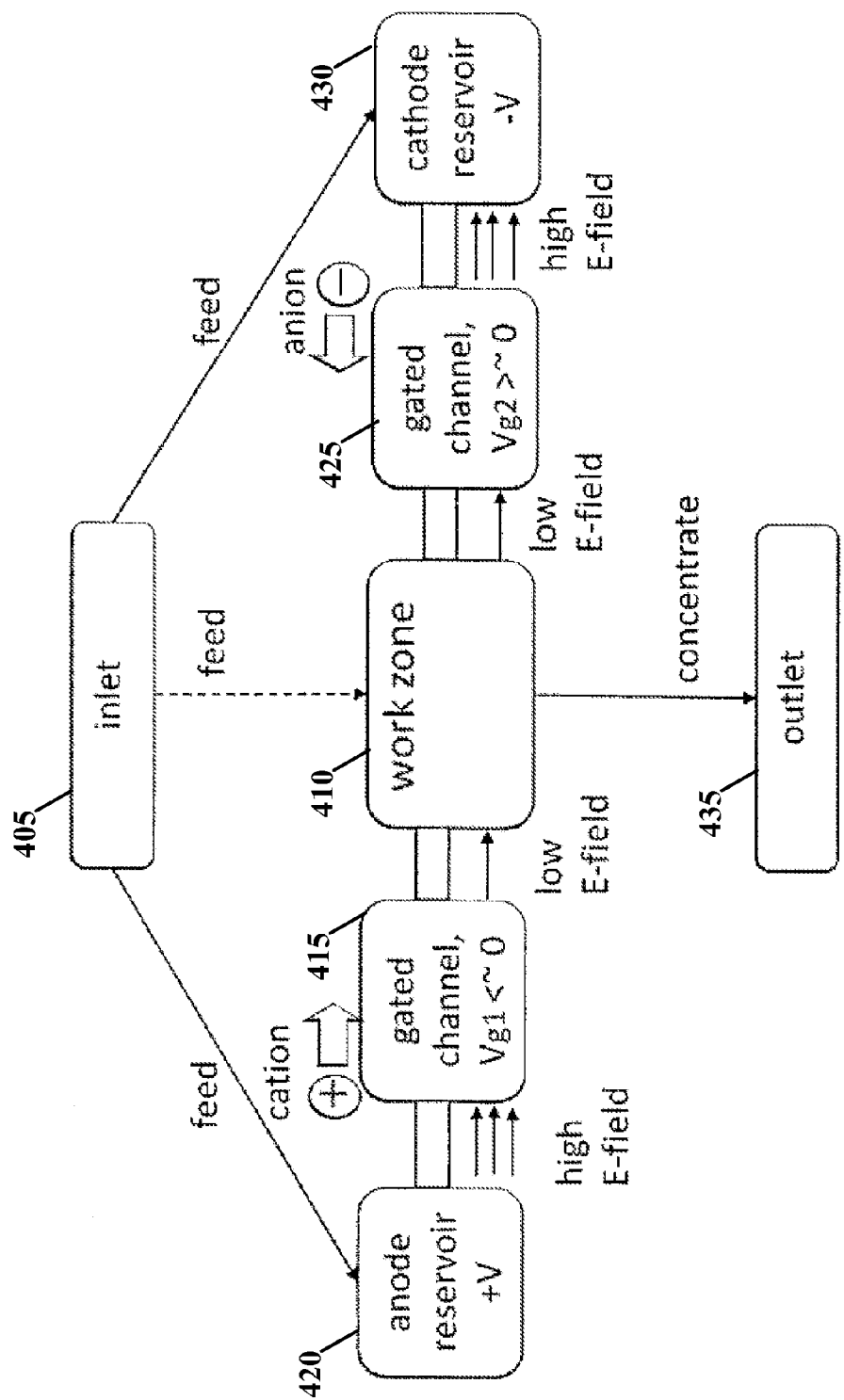
FIG. 4 shows an example diagram of concentration operation, consistent with various aspects of the present disclosure.

FIG. 4 shows an example diagram of concentration operation, consistent with various aspects of the present disclosure. The concentration operation occurs where the gate electrodes are properly biased so that minimum potential drop occurs between them, as opposed to the maximum drop as is used in operation of the device shown in FIG. 3. The resultant small electric between the gates therefore leads to accumulation of charged species within that zone due to ion flux continuity. The applications of this operation include the pre-concentration of biological samples. In FIG. 4, water fluid (including charged species such as biological molecules) is introduced at an inlet 405, and provided into a work zone 410. On opposing sides of the work zone 410, are a first gated channel 415 and a second gated channel 425 (each of which includes multiple porous structures as shown in further detail in FIG. 2). The first gated channel 415 connects the work zone 410 to an anode reservoir 420, and the second gated channel 425 connects the work zone 410 to a cathode reservoir 430.

The water fluid is processed in the work zone 410 by applying electric voltages to electrically bias the first porous structure by way of the gated channel 415 and the corresponding anode reservoir 420 with a first bias-polarity type ($V_{g1} < \sim 0$). Additionally, the electric voltages are applied to electrically bias the second porous structure by way of the gated channel 425 and the corresponding cathode reservoir 430 with a second bias-polarity type that is different than the first bias-polarity type ($V_{g2} > \sim 0$). Due to this biasing, a low electric field is created between each the work zone 410 and each of the gated channels 415/425. Further, a high electric field is respectively created between each of the gated channels 415/425 and the anode and cathode reservoirs 420/430. With cations and ions from the anode and cathode reservoirs 420/430 flowing toward the work zone 410, the charged species in the water fluid is concentrated, and can be collected for analysis at the outlet 435.

Figure 5:
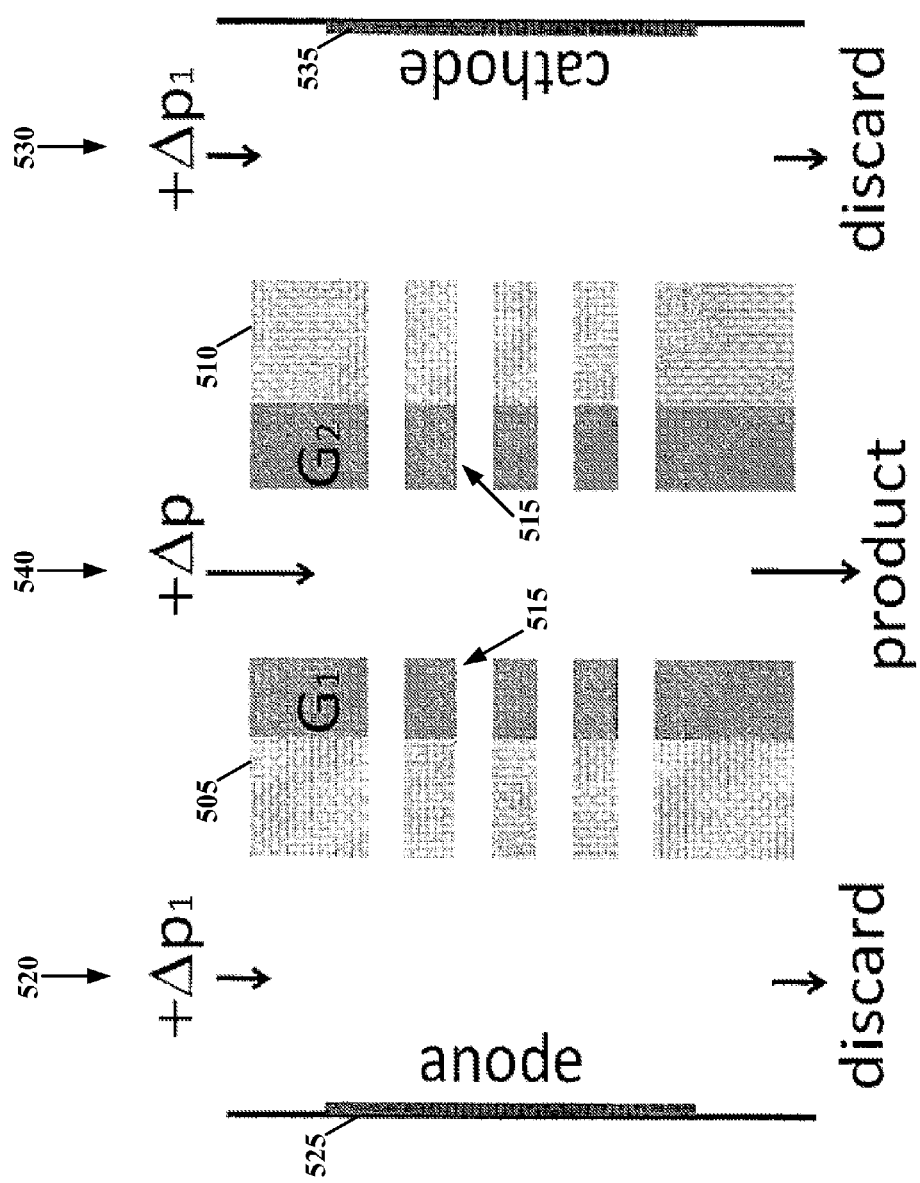
FIG. 5 shows an example illustration of a method of feeding bulk solution based on pressure-gradient in the longitudinal direction, consistent with various aspects of the present disclosure.

FIG. 5 shows an example illustration of a method of feeding bulk solution based on pressure-gradient in the longitudinal direction, consistent with various aspects of the present disclosure. In this particular case, small pressure gradient is also applied at the reservoir channels to maintain the bulk condition there. For instance, as shown in FIG. 5, a first porous structure 505 and a second porous structure 510 are included in the device shown, and both include gated channels 515. An anode reservoir 520 (a respective anode 525) and a cathode reservoir 530 (with a respective cathode 535) are also used. In between the first porous structure 505 and the second porous structure 510 is a work zone 540. Water fluid, which includes ionic minerals such as sodium chloride, is passed through the work zone 540 and results in a product that includes the water fluid screened of ionic minerals.

Electric voltages set to establish a sufficient voltage difference between the anode reservoir 520 and the cathode reservoir 530 to deplete sodium chloride ions in the water fluid in the work zone 540 due to ion-flux continuity. In this manner, sodium chloride anions are passed from the work zone 540 through the plurality of gated channels 515 of the first porous structure 505 to the anode reservoir 520. Sodium chloride cations are passed from the work zone 540 through the plurality of gated channels 515 of the second porous structure 510 to the cathode reservoir 530. As a result, ion-filtered water is collected as product from the work zone 540. The sodium chloride anions and the sodium chloride cations are discarded from the anode reservoir 520 and the cathode reservoir 530. The positive pressure gradient applied at each of the anode reservoir 520, the cathode reservoir 530, and the work zone 540. This allows for the injecting ionic minerals in the water fluid into the work zone 540 at a faster rate than sodium chloride cations and ions are passed from the work zone 540 through the plurality of gated channels 515.

Figure 6:
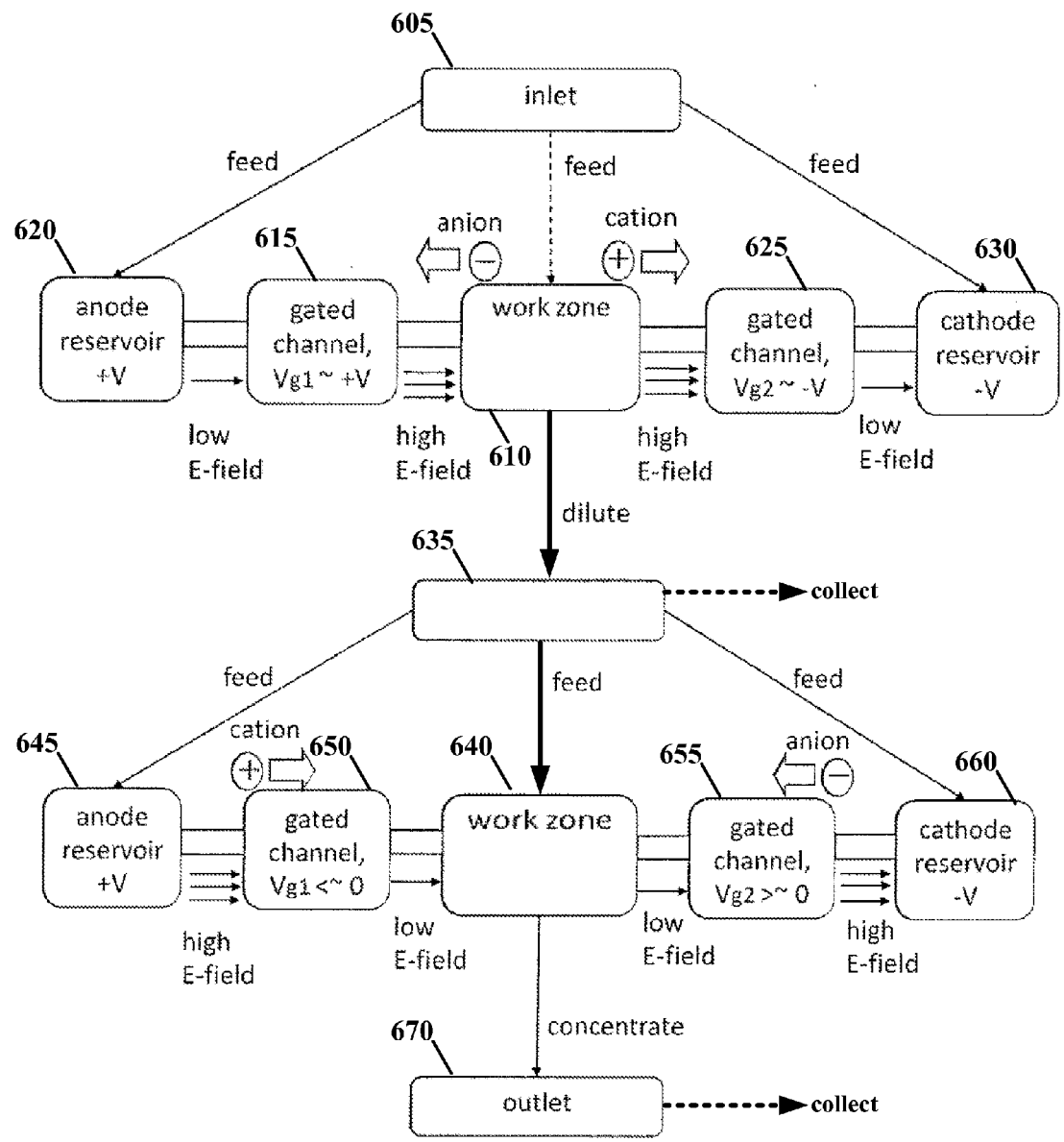
FIG. 6 shows an example tiered device diagram for diluting and concentrating aspects of a water solution, consistent with various aspects of the present disclosure.

In more specific implementations, the spacings within the work zone(s) and as provided by the porous structures can be set by testing for specific applications (and optionally, adaptively monitoring by testing as with the lower portion of FIG. 6 for adaptively varying such spacings as needed). As an example, the porous structures have their passage ways sufficiently sized to pass the ions therethrough without clogging. For example, an inner diameter of 100-500 nanometers is practical for applications in which other artifacts (e.g., biomolecules, macromolecules, oil droplets) are not in abundance. Similarly, the lateral spacing across the work zone (as illustrated) can be tested and set based on the bias (difference) voltage applied to the porous (gate) structures and the degree of concentration (e.g., of NaCl). In certain nonlimiting exemplary applications, the lateral spacing can be set to greater than a few to several hundred nanometers, and to spacing on the order of hundreds or thousands of nanometers as permitted by the applicable ionic flux.

FIG. 6 shows an example tiered device diagram for diluting and concentrating aspects of a water solution, consistent with various aspects of the present disclosure. In certain implementations, it may be advantageous to both filter unwanted ionic particles (such as sodium chloride) from a water fluid and also collect a charged particle that is in the water fluid for sample testing. Using the arrangement shown in FIG. 6, both dilution/filtering and concentration can occur. Water fluid is introduced at an inlet 605, and provided into a first work zone 610. A first gated channel 615 and a second gated channel 625 (each of which includes multiple porous structures as shown in further detail in FIG. 2) are located on either side of the first work zone 610. The first gated channel 615 connects the first work zone 610 to a first anode reservoir 620, and the second gated channel 625 connects the first work zone 610 to a first cathode reservoir 630.

The water fluid is processed/filtered in the first work zone 610 by applying electric voltages to electrically bias the first porous structure by way of the first gated channel 615 and the corresponding first anode reservoir 620 with a first bias-polarity type ($V_{g1}$~+V). Additionally, the electric voltages are applied to electrically bias the second porous structure by way of the second gated channel 625 and the corresponding first cathode reservoir 630 with a second bias-polarity type that is opposite the first bias-polarity type ($V_{g2}$~−V). A described in detail above with reference to FIG. 3, due to this biasing, the electric voltages establish a sufficient voltage difference between the first anode reservoir 620 and the first cathode reservoir 630 to deplete sodium chloride ions in the water fluid in the first work zone 610 due to ion-flux continuity, which is output at a first outlet 635. The water fluid can be collected at this time.

Subsequently, the water fluid as filtered by the filtering device (including charged species such as biological molecules) is introduced at from the first outlet 635, and provided into a second work zone 640. On opposing sides of the second work zone 640, are a third gated channel 650 and a fourth gated channel 655 (each of which includes multiple porous structures as shown in further detail in FIG. 2). The third gated channel 650 connects the second work zone 640 to a second anode reservoir 645, and the fourth gated channel 655 connects the second work zone 640 to a second cathode reservoir 660.

The water fluid is processed in the second work zone 640 by applying electric voltages to electrically bias the porous structure of the third gated channel 650 and the corresponding second anode reservoir 645 with a third bias-polarity type ($V_{g1}$<~0). Additionally, the electric voltages are applied to electrically bias the fourth porous structure of the gated channel 655 and the corresponding second cathode reservoir 660 with a fourth bias-polarity type that is different the third bias-polarity type ($V_{g2}$>~0). Due to this biasing, cations and ions from the second anode and second cathode reservoirs 645/660 flow toward the second work zone 640, and a targeted charged species in the water fluid is concentrated. The targeted charge species can be collected for analysis at the second outlet 670.

Although the arrangement of FIG. 6 shows dilution prior to concentration, the arrangement of the devices can be swapped as needed. Additionally, further devices can be used in conjunction if, for example, multiple different types of charged spies are to be diluted one or more dilution devices can be added to the arrangement shown. Similarly, one or more concentration devices can be added, or even a combination of both types of devices.

Figure 7:
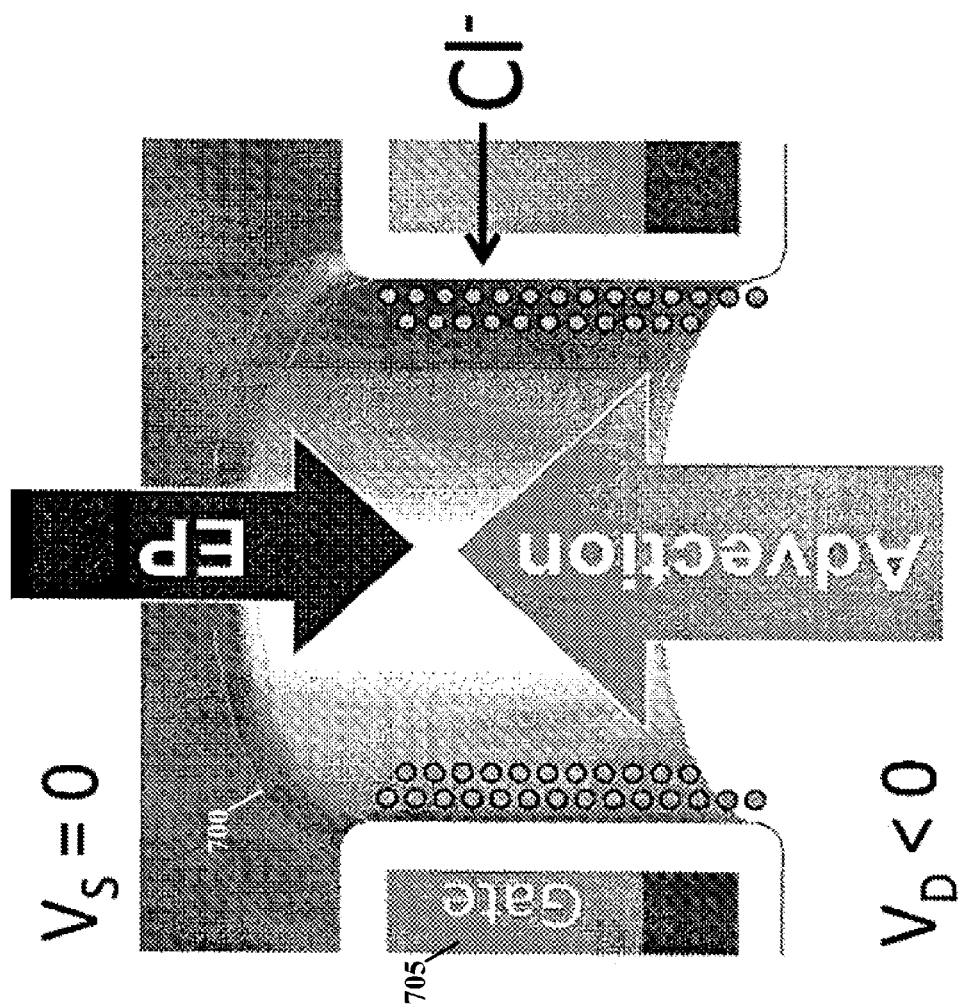
FIG. 7 shows an example schematic of an operation of a pore for selective filtering of molecules, consistent with various aspects of the present disclosure.

FIG. 7 shows an example schematic of an operation of a pore for selective filtering of molecules, consistent with various aspects of the present disclosure. The pore 700 can selectively filtering of proteins. The device can be operated at pH 7 where the surface of the pore is charged positively. The proteins that the pore manipulates are charged positively, thus requiring negative $V_D$ to translocate. The counter ions are oppose the electrophoretic flow of proteins. The operating principle remains identical to the demonstrated pore, once the charge polarities of all entities involved reverse. The gate 705 of the pore can be biased similar to the embodiments discussed above.

Based upon the above discussion and illustrations, those skilled in the art will readily recognize that various modifications and changes may be made without strictly following the exemplary embodiments and applications illustrated and described herein. Furthermore, various features of the different embodiments may be implemented in various combinations. Such modifications do not depart from the true spirit and scope of the present disclosure, including those set forth in the following claims.

What is claimed is:

1. A method for filtering water fluid by screening ionic minerals including sodium chloride from the water fluid, the method comprising:
passing the water fluid into a work zone defined at least in part by oppositely-arranged first and second porous structures, the first porous structure having a plurality of gated channels corresponding to an anode reservoir and the second porous structure having a plurality of gated channels corresponding to a cathode reservoir, wherein the gated channels include channels having gates with gate electrodes along sides of the channels;
processing the water fluid in the work zone by,
applying respective electric voltages to electrically bias,
the first porous structure and the corresponding anode reservoir with a first bias-polarity type by way of the plurality of gated channels corresponding to the anode reservoir and
the second porous structure and the corresponding cathode reservoir with a second bias-polarity type that is opposite the first bias-polarity type by way of the plurality of gated channels corresponding to the cathode reservoir, the respective electric voltages being set to establish a sufficient voltage difference therebetween to deplete sodium chloride ions in the water fluid in the work zone due to ion-flux continuity, whereby sodium chloride anions are passed from the work zone through the plurality of gated channels of the first porous structure to the anode reservoir, and sodium chloride cations are passed from the work zone through the plurality of gated channels of the second porous structure to the cathode reservoir; and
collecting, in response to the step of processing, ion-depleted water from the work zone.

2. The method of claim 1, further including the steps of providing the water fluid in the cathode reservoir and anode reservoir during the step of processing the water fluid in the work zone, and providing the ion-depleted water from the work zone that is desalinated or purified for human consumption.

3. The method of claim 1, further including the step of replenishing the cathode reservoir and the anode reservoir with additional water fluid to maintain a bulk ionic condition of fluid in each of the cathode reservoir and the anode reservoir.

4. The method of claim 1, further including the step of replenishing the cathode reservoir and the anode reservoir with additional water fluid to maintain a bulk ionic condition of fluid in each of the cathode reservoir and the anode reservoir, and wherein a size of the plurality of gated channels corresponding to the cathode and anode reservoir is not limited by the Debye screening length.

5. The method of claim 1, further including the step of replenishing the cathode reservoir and the anode reservoir with additional water fluid by using a pressure differential, that defines pressure of the water fluid passed to the reservoirs relative to pressure of fluid passed to the work zone, to maintain a bulk ionic condition of the fluid in each of the cathode reservoir and the anode reservoir.

6. The method of claim 1, wherein the porous structures are configured and arranged to control movement of the sodium chloride ions under the influence of an electric field, through the pores and thereby maintain a range of ionic concentration in the work zone that is within fifteen percent of a target value.

7. The method of claim 1, wherein the water fluid includes seawater manifesting sodium chloride at levels of between a range of 200-500 millimolar, and wherein the porous structures are sufficiently sized to pass the ions therethrough without clogging the porous structures.

8. The method of claim 1, wherein the water fluid includes seawater manifesting sodium chloride at levels of between a range of 400-500 millimolar, and wherein the porous structures are sufficiently sized to pass the ions therethrough without clogging the porous structures.

9. The method of claim 1, wherein the water fluid includes seawater manifesting sodium chloride at levels of between a range of 200-500 millimolar, wherein the porous structures are sufficiently sized to pass the ions therethrough without clogging the porous structures, and wherein the step of collecting including providing the ion-depleted water with sodium chloride at levels in a range that is between 0.35 mM to 1.3 mM.

10. The method of claim 1, further including passing the water fluid through an inlet to the work zone and an outlet at which the ion-depleted water is collected, and further including processing the water fluid in the work zone by applying the respective electric voltages, in combination at least one of a pressure-difference control technique and electro-osmosis, to control particle electrophoresis through the pores and thereby maintain a selected concentration of sodium chloride ions in the work zone.

11. The method of claim 1, further including the step of filtering from the water fluid at least one of: oil droplets, macromolecules, biological ions, ionic species, and potassium.

12. The method of claim 1, wherein applying the respective electric voltages includes controlling electrostatic potential within the gated channels of the porous structures and in the work zone via extended field effect that is not limited by the Debye screening length.

13. The method of claim 1, wherein applying the respective electric voltages includes injecting the ionic minerals in the water fluid into the work zone at a faster rate than sodium chloride cations are passed from the work zone through the plurality of gated channels of the second porous structure.

14. The method of claim 1, wherein applying the respective electric voltages includes injecting the ionic minerals in the water fluid into the work zone at a faster rate than sodium chloride anions are passed from the work zone through the plurality of gated channels of the first porous structure.

15. The method of claim 1, wherein applying the respective electric voltages includes injecting the ionic minerals in the water fluid into the work zone at a faster rate than sodium chloride cations are passed from the work zone through the plurality of gated channels of the second porous structure and at a faster rate than sodium chloride anions are passed from the work zone through the plurality of gated channels of the first porous structure.

16. A water-filtering apparatus, comprising:
a water processing station configured and arranged to process water fluid having ionic minerals therein including sodium chloride, in a work zone defined at least in part by oppositely-arranged first and second porous structures, the first porous structure having a plurality of gated channels corresponding to an anode reservoir and the second porous structure having a plurality of gated channels corresponding to a cathode reservoir, wherein the gated channels include channels having gates with gate electrodes along sides of the channels;
an anode reservoir station including an anode and the anode reservoir;
a cathode reservoir station including a cathode and the cathode reservoir;
a power source configured and arranged to apply respective electric voltages, while the water fluid is in the work zone by applying respective electric voltages to electrically bias,
  the first porous structure and the corresponding anode reservoir with a first bias-polarity type by way of the plurality of gated channels corresponding to the anode reservoir, and
  the second porous structure and the corresponding cathode reservoir with a second bias-polarity type that is opposite the first bias-polarity type by way of the gated channels corresponding to the cathode reservoir,
  the respective electric voltages being set to establish a sufficient voltage difference therebetween to deplete sodium chloride ions in the water fluid in the work zone due to ion-flux continuity, whereby sodium chloride anions are passed from the work zone through the plurality of gated channels of the first porous structure to the anode reservoir, and sodium chloride cations are passed from the work zone through the plurality of gated channels of the second porous structure to the cathode reservoir; and
a water collection station configured and arranged to receive ion-depleted water from the work zone.

17. The apparatus of claim 16, further including:
a separate filtering apparatus configured and arranged for filtering from the water fluid at least one of: oil droplets, macromolecules, biological ions, ionic species, and potassium, and
wherein the gate electrodes of the gated channels corresponding to the anode reservoir and the gate electrodes of the gated channels corresponding to the cathode reservoir are biased with the first and second biased-polarity types, respectively, by applying a first electric voltage to the gate electrodes of the gated channels corresponding to the anode reservoir and applying a second electric voltage to the gate electrodes of the gated channels corresponding to the cathode reservoir.

18. The apparatus of claim 16, further including an inlet and outlet to the water processing station, wherein the water fluid is driven from the inlet to the outlet either by pressure difference or electro-osmosis, and through the work zone, the ionic minerals concentration is increased, and collected at the water collection station as product.

19. The apparatus of claim 16, further including an inlet and outlet to the water processing station, wherein the water fluid is driven from the inlet to the outlet either by pressure difference or electro-osmosis, and through the work zone, the ionic minerals concentration is decreased, and collected at the water collection station as product.

20. The apparatus of claim 16, wherein the water fluid includes seawater manifesting sodium chloride at levels of between with a range of 200-500 millimolar, and wherein the porous structures are sufficiently sized to pass the ions therethrough without clogging the porous structures.

21. An apparatus for filtering water fluid by screening ionic minerals including sodium chloride from the water fluid, the apparatus comprising:

water processing station configured and arranged to pass the water fluid into a work zone defined at least in part by oppositely-arranged first and second porous structures, the first porous structure having a plurality of gated channels corresponding to an anode reservoir and the second porous structure having a plurality of gated channels corresponding to a cathode reservoir, wherein the gated channels include channels having gates along sides of the channels and the water processing station includes each of the gated channels and is located in the work zone;

a power source configured and arranged to process the water fluid in the work zone by, applying respective electric voltages to electrically bias, the first porous structure and the corresponding anode reservoir with a first bias-polarity type by way of the plurality of gated channels corresponding to the anode reservoir and the second porous structure and the corresponding cathode reservoir with a second bias-polarity type that is opposite the first bias-polarity type by way of the plurality of gated channels corresponding to the cathode reservoir, the respective electric voltages being set to establish a sufficient voltage difference therebetween to deplete sodium chloride ions in the water fluid in the work zone due to ion-flux continuity, whereby sodium chloride anions are passed from the work zone through the plurality of gated channels of the first porous structure to the anode reservoir, and sodium chloride cations are passed from the work zone through the plurality of gated channels of the second porous structure to the cathode reservoir; and water collection station configured and arranged to receive, in response to the step of processing, ion-depleted water from the work zone.

* * * * *